United States Patent [19]

Lind

[11] 4,072,892
[45] Feb. 7, 1978

[54] ELECTROLYTIC MEASUREMENT SYSTEM WITH AN INNER POST AND AN OUTER CYLINDRICAL SHIELD FLUID BOUNDARY

[75] Inventor: Earl R. Lind, Portsmouth, R.I.

[73] Assignee: Raytheon Company, Lexington, Mass.

[21] Appl. No.: 772,362

[22] Filed: Feb. 22, 1977

Related U.S. Application Data

[63] Continuation of Ser. No. 644,499, Dec. 29, 1975, abandoned.

[51] Int. Cl.² ............................................. G01N 27/42
[52] U.S. Cl. .................................... 324/30 B; 204/272
[58] Field of Search ............................ 324/30 R, 30 B; 204/195 R, 269, 272

[56] References Cited

U.S. PATENT DOCUMENTS

| | | | |
|---|---|---|---|
| 2,764,540 | 9/1956 | Farin et al. | 204/272 |
| 3,701,006 | 10/1972 | Volkel | 324/30 R |
| 3,905,885 | 9/1975 | Bengel | 204/272 |

*Primary Examiner*—Rudolph V. Rolinec
*Assistant Examiner*—Michael J. Tokar
*Attorney, Agent, or Firm*—David M. Warren; Milton D. Bartlett; Joseph D. Pannone

[57] ABSTRACT

An electrolytic measurement system incorporating a probe for the measurement of the conductivity of fluids such as sewage and other industrial effluents. The probe has a smooth surface to passage of the fluid with flush-mounted electrodes arranged serially along the passage. The passage is formed within material that is an electrical insulator and is surrounded by a metallic shield symmetrically positioned with respect to the ends of the serially arranged electrodes. An electric potential is impressed between the outer electrodes and the shield, the latter being grounded, while an inner electrode is used for the measurement of electric current flowing through the fluid from the outer electrodes to the inner electrode. Sensing electrodes positioned between the inner and outer electrodes are utilized in a feedback circuit for sensing the electric field to vary the magnitude of the impressed voltage to maintain a constant magnitude of impressed field independently of the presence of electrochemical byproducts upon the electrode surfaces.

4 Claims, 1 Drawing Figure

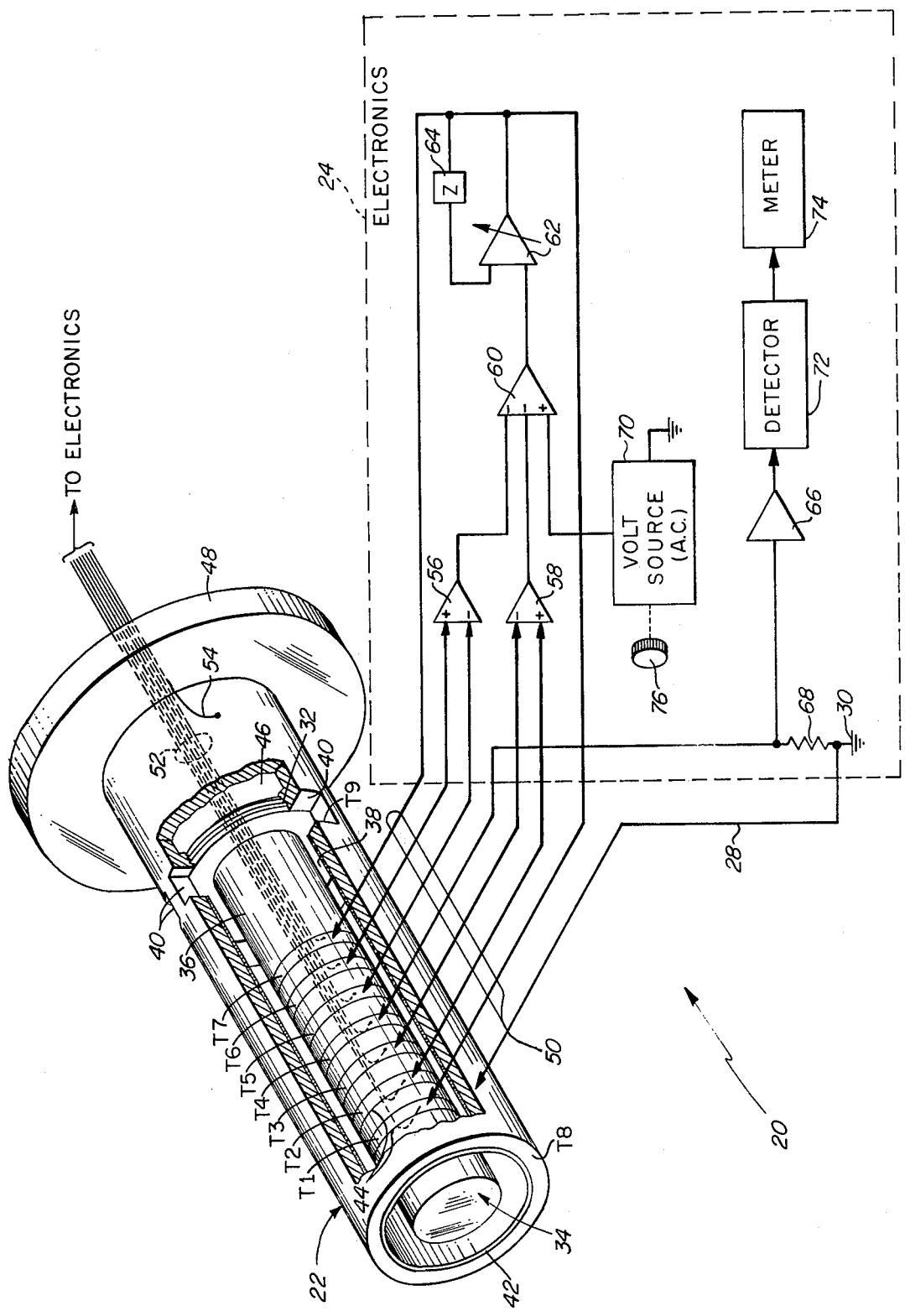

ELECTROLYTIC MEASUREMENT SYSTEM WITH AN INNER POST AND AN OUTER CYLINDRICAL SHIELD FLUID BOUNDARY

CROSS-REFERENCE TO RELATED CASES

This is a continuation of application Ser. No. 644,499, filed Dec. 29, 1975, now abandoned.

BACKGROUND OF THE INVENTION

Electrolytic measurement systems employ probes having electrodes which are immersed in a fluid for measuring the electrical conductivity thereof. Such probes are often immersed in sewage or industrial effluents having chemical substances which react under the influence of electric fields within the probe to produce electrochemical encrustations upon the electrodes as well as upon a metallic shield or a case which may be used to shape the electric fields and control ground currents to permit a more precise measurement of the fluid characteristics. For example, in the case of a saline solution, the electrical conductivity of the fluid is a measure of the concentration of ions in solution.

There are two problems that are frequently encountered in the measurement of the electrical conductivity of fluids. First, particularly in the case of raw sewage, there is a tendency for probes immersed in the sewage to clog because of hairs, threads, and other vegetable and animal matter which may become entrapped in the probe and prevent the passage of fluid therethrough. Secondly, the aforementioned electrochemical by-products tend to precipitate on the surfaces of the electrodes and introduce an electrode resistance thereto with the result that the distribution of electric fields between individual ones of the electrodes as well as between the electrodes and the shield is altered. Furthermore, the electrode resistance induced by the encrustation alters the magnitudes of currents flowing through the fluid with a resultant loss of calibration of the measurement system.

SUMMARY OF THE INVENTION

The aforementioned problems are overcome and other advantages are provided by an electrolytic measurement system which measures the electrical conductivity of fluids, is resistant to clogging, and provides measurements that are substantially independent of electrochemical precipitates which may form upon the surface of electrodes. In accordance with the invention, the electrolytic measurement system incorporates a probe having a smoothly surfaced passage for fluid, the boundary of the passage being formed of electrically insulating material and having a cylindrical shape with electrodes arranged serially along the passage and mounted flush within the walls to permit matter suspended within the fluid to pass by the walls without adhering thereto. Furthermore, the invention may employ a metallic shield mounted externally to the cylindrical walls of the passage and symmetrically positioned with respect to the arrangement of the serially positioned electrodes to form an electric field configuration which is substantially invariant as to the aforementioned precipitates.

In a preferred embodiment of the invention, the outer electrodes of the arrangement of electrodes are positioned adjacent the ends of the shield while an inner electrode, positioned in the middle of the array of electrodes, is located opposite the center of the shield. A feedback circuit impresses a voltage between each of the outer electrodes and the shield, the latter being grounded. The inner electrode is connected by a resistor to ground to measure current flowing between each of the outer electrodes and the inner electrode through a fluid which may be present in the passage. The current is a measure of the conductivity of the fluid when the electric field impressed through the fluid between the outer and inner electrodes has a predetermined value. Sensing electrodes are placed between the inner and outer electrodes to measure this electric field, the sensing electrodes being coupled to the feedback circuit for varying the voltage impressed upon the outer electrodes to compensate for changes in electrode resistance due to electrochemical precipitates. The compensation for the changes in electrode resistance provides for a constant value of electric field impressed through the fluid so that an accurate measurement of fluid conductivity is obtained.

The external shield is particularly useful in those situations wherein the probe is mounted in close proximity to other sensors since the shield prevents electric fields from the other sensors and from the probe from interfering respectively with the operation of the probe and the other sensors. In the absence of external sources of electric field, or sensors sensitive to electric fields, the shield may be omitted.

BRIEF DESCRIPTION OF THE DRAWING

The aforementioned aspects and other features of the invention are explained in the following description taken in connection with the accompanying drawing which shows the probe and its connection with the feedback circuit in accordance with the invention.

DESCRIPTION OF THE PREFERRED EMBODIMENT

Referring now to the FIGURE, there is seen a diagram of a system 20 of an electrolytic measurement system which, in accordance with the invention, has a probe 22, shown in an isometric view partially cut away to expose the interior portions thereof, coupled to an electronics unit 24, shown schematically. The probe 22 comprises a cylindrical metallic shield 26 which is grounded via line 28 to ground 30 within the electronics unit 24. The shield 26 is threadedly secured via threads 32 to a post 34 having a cylindrical surface 36 which serves as the inner surface of a passage 38 through which fluid flows by entering at the bottom of the probe 22 and exiting through ports 40 near the upper end of the probe 22. The outer surface of the passage 38 is formed by a liner 42 adhesively secured to the inner surface of the shield 26. Both the post 34 and the liner 42 are fabricated from material which is electrically insulating such as polyvinyl chloride or an epoxy.

Electrodes for impressing an electric field through fluid flowing in the passage 38 may be placed along the inner surface or outer surface or on both the inner and the outer surfaces of the boundary of the passage 38. In the embodiment shown in the FIGURE, electrodes 44 are shown flush-mounted to the surface of the post 34, there being seven electrodes 44 in this embodiment of the invention with the electrodes 44 being further identified in the FIGURE by the symbols T1–T7. The bottom and top positions of the electrically conducting shield 26 are also identified in the FIGURE by the legends T8 and T9 to facilitate the description of the electric field between individual ones of the electrodes 44 and between the electrodes 44 and the bottom and top portions of the shield 26.

The post 34 has an enlarged top portion 46, the lower surface of which forms the upper boundary of the passage 38 and directs fluid through the ports 40. The top portion 46 also contains the aforementioned threads 32 for securing the post 34 to the shield 26. In addition, the top portion 46 is provided with a lip 48 which extends outwardly beyond the shield 26 and serves to support the probe 22 as, for example, by suspending the probe 22 through an aperture in a tank, not shown in the FIGURE, containing the fluid of which the conductivity is to be measured.

The seven electrodes 44 are symmetrically positioned with respect to the portion of the shield 26 located between T8 and T9 with the electrode T4 being positioned adjacent the midpoint of the liner 42. The electrodes 44 are shown coupled to the electronics unit 24 schematically via lines 50 while wires 52 are provided for physically connecting the electrodes 44 to the electronics unit 24. In fabricating the post 34, the electrodes 44 and the wires 52 are supported by a jig while an epoxy is forced into the jig between the electrodes 44 and the wires 52 and allowed to solidify. An additional wire 54 is coupled to the shield 26 to provide for the grounding of the shield 26 to ground 30 as is represented schematically by the line 28.

The electronics unit 24 comprises four differential amplifiers 56, 58, 60 and 62, an impedance network 64 coupled in feedback arrangement to the amplifier 62, an amplifier 66, a resistor 68 coupled between electrode T4 and ground 30, a source 70 of voltage, a detector 72 and a meter 74.

The source 70 applies a voltage via amplifiers 60 and 62 to the electrodes T1 and T7 for exciting an electric field between the electrode T1 and the portion T8 of the shield 26 as well as between the electrode T7 and the portion T9. Since the electrode T4 is grounded by the resistor 68, an electric field is also established between the electrodes T1 and T4 as well as between the electrodes T7 and T4. An electric current flows through the resistor 68 and has a magnitude dependent on the magnitudes of the electric field between the electrodes T1 and T4 and the electric field between the electrodes T7 and T4. The current is also dependent on the electrical conductivity of a fluid passing through the passage 38 and on the resistances of the electrodes T1, T4 and T7, particularly the resistance of any encrustations or precipitates of materials on these electrodes produced by electrochemical reactions of substances within the fluid in the passage 38 under the influence of the aforementioned electric fields.

The current established in the resistors 68 through energization of the circuit by the source 70 serves as a measure of the conductivity of the fluid when the electric fields established therein are of a predetermined value. While the current in the resistor 68 may be either a direct current (DC) or an alternating current (AC), the alternating current is preferred because it prevents the polarization of the electrodes 44 as has been found to occur when direct current is utilized. The polarization occurs by virtue of electrochemical reactions at the surfaces of the electrodes 44, and serves as additional sources of electric fields which degrade the accuracy of the conductivity measurement. Accordingly, the voltage source 70 is an AC source such as an oscillator with a variable frequency control to permit setting the frequency of oscillation at a frequency within the bandwidth of the feedback circuit to be described below.

In order to maintain the sum of the electric field in the fluid between the electrodes T1 and T4 and the electric field in the fluid between the electrodes T7 and T4 at a constant predetermined magnitude, the magnitude being the peak value of the AC signal, the electrodes 44 positioned between the inner electrode T4 and the outer electrodes T1 and T7 are utilized to sense the electric field strength for providing signals to the amplifiers 56 and 58. The amplifiers 56 and 58 are connected in a feedback circuit with the source 70 via the differential input terminals of the amplifier 60 to maintain a fixed ratio between the magnitude of the sum of electric fields and the magnitude of the voltage of the source 70. The magnitude of the voltage provided by the source 70 is adjusted by means of a knob 76. By virtue of the feedback arrangement, the magnitude of the sum of the electric fields in the fluid is readily set to a desired value by turning the knob 76, the feedback arrangement insuring that the preset value of the sum of the electric fields is maintained.

The electrodes T6 and T5 sense the amplitude of the electric field between the electrodes T4 and T7 while the electrodes T2 and T3 sense the magnitude of the electric field between the electrodes T4 and T1. The electrodes T6 and T5 are coupled respectively to the plus and minus input terminals of the amplifier 56 while the electrodes T2 and T3 are coupled respectively to the plus and minus input terminals of the amplifier 58. The input impedances of the amplifiers 56 and 58 are of a sufficiently high value that negligible current is drawn by these amplifiers from the terminals T6, T5, T2 and T3. The output signals of the amplifiers 56 and 58 are summed together at the minus input terminals of the amplifier 60, it being understood that the amplifier 60 includes suitable summing resistors (not shown) for combining the signals of the amplifiers 56 and 58. The amplifier 62 which couples the output of the amplifier 60 to the terminals T1 and T7 has a variable gain which can be manually set to a suitable value for insuring the stability of the overall feedback loop, the minor feedback loop around the amplifier 62 via the impedance network 64 providing filtering which insures stability of the overall feedback loop. The impedance network 64 typically comprises one or more resistors and capacitors as is well known in the art of feedback circuits. The loop error signal, namely, the difference between the magnitude of the voltage of the source 70 applied to the plus input terminal of the amplifier 60 and the signals of the amplifiers 56 and 58 applied to the minus input terminals of the amplifier 60, is kept to a small value independently of the aforementioned electrode resistance due to precipitates on the electrodes 44.

The minus input terminals of the amplifiers 56 and 58 are coupled to electrodes 44 adjacent the inner electrode T4 while the plus input terminals of the amplifiers 56 and 58 are coupled to electrodes 44 adjacent the outer electrodes T7 and T1, this symmetry of coupling being utilized because of the symmetrical orientation of the electric fields in the passage 38. For example, when the electrode T7 is excited by a positive voltage, the electrode T1 is also excited by the same positive voltage with the result that the electric fields are directed from the electrode T7 and T1 to the electrode T4; thus, one electric field direction is the same as that of the flow of fluid while the other electric field goes countercurrent to the flow of fluid.

The voltage appearing across the resistor 68 is amplified by the amplifier 66 and applied to a detector 72 which detects the peak voltage of the AC signal provided by the amplifier 66. The output of the detector 72 is then applied to the meter 74 which is calibrated to read the conductivity of the fluid in the passage 38.

In operation, therefore, the difference in potential between the electrodes T6 and T5 induced therein by the electric field impressed between electrodes T7 and T4 is sensed by the differential amplifier 56. Similarly, the difference or potential between the electrodes T2 and T3 induced therein by the electric field from electrode T1 to electrode T4 is sensed by the differential amplifier 58. The output signals of the amplifiers 56 and 58 serve as a feedback signal in the feedback loop which constrains the feedback signal to equal the voltage of the source 70. The feedback loop varies the magnitude of the voltage impressed upon electrodes T1 and T7 in accordance with variations in the terminal resistance of the electrodes 44 brought on by electrochemical reactions so that the sum of the electric fields is not affected by these electrochemical reactions. The arrangement of the electrodes 44 relative to the insulating liner 42 and the shield 26 has symmetry which provides symmetry to the electric field pattern. Ground currents flowing from the electrode T7 through the fluid to the shield portion T9 as well as ground currents flowing from the electrode T1 to the shield portion T8 remain away from the vicinity of the electrode T4 wherein the measurement of conductivity is made. The shield 26 prevents various electric currents and electric fields of sources external to the probe 22 from reaching the vicinity of the inner electrode T4 where the conductivity measurements are are made. In this way, the region wherein the conductivity measurements are made is protected by a pattern electric field which is invariant to encrustation of the electrodes 44 from electrochemical reactions. Also, electric fields of predetermined directions and predetermined magnitudes are maintained within the region where the conductivity measurements are made independently of encrustation of the electrodes 44 by electrochemical reactions.

It is understood that the above described embodiment of the invention is illustrative only and that modifications thereof may occur to those skilled in the art. Accordingly, it is desired that this invention is not to be limited to the embodiment disclosed herein but is to be limited only as defined by the appended claims.

What is claimed is:

1. An electrolytic measurement system comprising:
    a passage for fluid having a boundary formed of an inner post and an outer cylindrical shield;
    a plurality of electrodes flush-mounted along the surface of said post within said boundary for making contact with said fluid, said electrodes being positioned in a serial arrangement along an axis of said passage;
    means for electrically energizing a plurality of outer ones of said electrodes which are symmetrically positioned about a center of said arrangement;
    means including pairs of said electrodes symmetically positioned between said outer electrodes and an inner one of said electrodes for signaling the presence of an electric current flowing between said outer electrodes and said inner electrode, said signaling means being coupled to said energizing means for maintaining a constant magnitude of electric field between said outer electrodes and said inner electrode independently of electrode resistance of said inner and outer electrodes;
    means coupled between said outer electrodes and said inner electrode for measuring electric current flow between said outer electrodes and said inner electrode.

2. A system according to claim 1 further comprising a grounded shield which is symmetrically positioned relative to said outer electrodes, encloses said plurality of electrodes, and is positioned outside of said boundary of said passage, said boundary being formed of an electrically insulating material.

3. A system according to claim 2 wherein said outer electrodes are energized with equal values of voltage relative to said grounded shield.

4. A probe for fluid measurement comprising:
    an elongated passage for conducting a fluid in the direction of an axis of said passage for measurement of a characteristic of said fluid, said passage being constructed of walls of an electrically insulating material and having a smooth surface for contacting said fluid;
    a plurality of electrodes arranged serially along said axis of said passage and mounted upon one of said walls for coupling electrical signals to said fluid;
    means electrically coupled to an inner electrode of said serially arranged electrodes for measuring an electric field in a central portion of said serially arranged electrodes;
    means for electrically shielding said inner electrode, said shielding means including first and second pairs of said electrodes symmetrically positioned about said inner electrode and being insulated from the central portion of said serially arranged electrodes; and
    means for electrically exciting a plurality of outer electrodes of said serially arranged electrodes which are symmetrically positioned about said inner electrode and said shielding means for establishing electric field lines which are directed in opposite directions about said central portion of said serially arranged electrodes and terminate on said shielding means.

* * * * *